US009169319B2

(12) United States Patent
Alarcon et al.

(10) Patent No.: US 9,169,319 B2
(45) Date of Patent: Oct. 27, 2015

(54) TARGETED ENZYMATIC DEGRADATION OF QUORUM-SENSING PEPTIDES

(71) Applicant: KCI Licensing, Inc., San Antonio, TX (US)

(72) Inventors: Rodolfo Alarcon, San Antonio, TX (US); Amy K. McNulty, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/841,200

(22) Filed: Mar. 15, 2013

(65) Prior Publication Data

US 2013/0253382 A1    Sep. 26, 2013

Related U.S. Application Data

(60) Provisional application No. 61/613,306, filed on Mar. 20, 2012.

(51) Int. Cl.
| | |
|---|---|
| *A61K 38/48* | (2006.01) |
| *C07K 16/12* | (2006.01) |
| *A61K 39/395* | (2006.01) |
| *C07K 14/00* | (2006.01) |
| *A61M 1/00* | (2006.01) |
| *A61L 29/16* | (2006.01) |

(52) U.S. Cl.
CPC ............... *C07K 16/12* (2013.01); *A61K 38/48* (2013.01); *A61K 39/395* (2013.01); *A61L 29/16* (2013.01); *A61M 1/00* (2013.01); *C07K 14/001* (2013.01); *A61L 2300/404* (2013.01)

(58) Field of Classification Search
CPC .................................................... A61K 38/48
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |

(Continued)

FOREIGN PATENT DOCUMENTS

| | | | |
|---|---|---|---|
| AU | 550575 A1 | 3/1986 | |
| AU | 745271 | 4/1999 | |

(Continued)

OTHER PUBLICATIONS

Schipper et al., 2009, Metagenome-Derived Clones Encoding Two Novel Lactonase Family Proteins Involved in Biofilm Inhibition in *Pseudomonas aeruginosa*, Applied and Environmental Microbiology, 75(1): 224-233.*

Camps et al., 2011, Paraoxonases as Potential Antibiofilm Agents: Their Relationship with Quorum-Sensing Signals in Gram-Negative Bacteria, Antimicrobial Agents and Chemotherapy, 5594): 1325-1331.*

International Search Report and Written Opinion for corresponding PCT/US2013/032500, mailed Jun. 24, 2013.

(Continued)

*Primary Examiner* — Amber D Steele

(57) ABSTRACT

Methods and compositions for the treatment of biofilms and/or the inhibition of biofilm formation. In one embodiment, a biofilm is treated and/or biofilm formation is inhibited by a method comprising contacting a biofilm or a surface with a bifunctional ligand comprising a quorum-sensing-peptide-binding region and a protease-binding region, whereby the biofilm is treated and/or biofilm formation on the surface is inhibited.

15 Claims, 2 Drawing Sheets

(56) References Cited

U.S. PATENT DOCUMENTS

| | | |
|---|---|---|
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,825,268 B2 | 11/2010 | Stumpe et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0166030 A1* | 9/2003 | O'Toole et al. .............. 435/7.32 |
| 2006/0079852 A1 | 4/2006 | Bubb et al. |
| 2006/0269951 A1* | 11/2006 | Taga et al. .................... 435/6 |
| 2008/0075730 A1* | 3/2008 | Storey et al. ............ 424/164.1 |
| 2009/0326416 A1* | 12/2009 | McNulty et al. ............ 600/573 |
| 2010/0111976 A1* | 5/2010 | Imboden et al. ......... 424/178.1 |
| 2011/0207657 A1* | 8/2011 | Eckert et al. ................. 514/2.6 |
| 2011/0212860 A1* | 9/2011 | Blackwell et al. ............ 506/15 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99113793 | 3/1999 |
| WO | WO 01/94543 A2 | 12/2001 |
| WO | WO 2009/114810 A2 | 9/2009 |
| WO | WO 2011/071904 A2 | 6/2011 |

OTHER PUBLICATIONS

Storz Michael P. et al: "Validation of PqsD as an Anti-biofilm Target in *Pseudomonas aeruginosa* by Development of Small-Molecule Inhibitors.", Journal of the American Chemical Society, Oct. 3, 2012, vol. 134, No. 39, pp. 16143-16146, XP002698484, ISSN:1520-5126 the whole document.

Dong Y-H et al: "Quorum-quenching microbial infections: mechanisms and implications." Jul. 29, 2007, Philosophical Transactions of the Royal Society of London. Series B, Biological Sciences, vol. 362, NR. 1483, pp. 1201-1211, XP002698485, ISSN: 0962-8436 abstract.

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

(56) References Cited

OTHER PUBLICATIONS

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines"), 19 pages.
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007), 92 pages.

\* cited by examiner

TARGETED ENZYMATIC DEGRADATION OF QUORUM-SENSING PEPTIDES

CROSS-REFERENCE TO RELATED APPLICATIONS

This application claims priority benefit of U.S. Provisional Patent Application No. 61/613,306 entitled, "TARGETED ENZYMATIC DEGRADATION OF QUORUM-SENSING PEPTIDES," filed Mar. 20, 2012, the disclosure of which is hereby incorporated herein by reference.

FIELD

The present invention relates generally to the fields of microbiology and wound care. More particularly, it concerns methods and compositions for inhibiting biofilms in wounds and on medical devices.

BACKGROUND

Infections due to biofilm growth formation are common complications of wound healing and surgical procedures, particularly in patients with devitalized tissue and decreased immunity. A biofilm forms when microorganisms, such as bacteria, fungi, yeast, protozoa, adhere to each other and to a surface, and produce extracellular polymers that facilitate adhesion and provide a structural matrix. Biofilms may form on living tissue or inert, nonliving material.

Biofilm-associated microorganisms behave differently from planktonic organisms. In particular, biofilms are characterized by their ability to become increasingly resistant to antimicrobial treatments. Accordingly, there is a need for methods and compositions that can be used in the treatment of biofilms and/or in inhibiting the formation of biofilms.

SUMMARY

The present invention provides methods and compositions for the treatment of biofilms and/or the inhibition of biofilm formation. In one embodiment, the present invention provides a method for treating a biofilm and/or inhibiting biofilm formation comprising contacting a biofilm or a surface with a bifunctional ligand comprising a quorum-sensing-peptide-binding region and a protease-binding region, whereby the biofilm is treated and/or biofilm formation on the surface is inhibited. In various embodiments the biofilm may be located on a surface, such as a surgical instrument, infected hardware, or an implanted device, including an indwelling medical device such as a catheter or a ventilation tube, and the tissue may be in contact with the device. In some embodiments, the patient is a human patient.

In certain embodiments, the method comprises contacting the biofilm or the surface with two or more bifunctional ligands. The two or more bifunctional ligands may be applied simultaneously or consecutively. The method further comprises contacting the surface with a protease, an antibiotic, or a combination thereof. The surface may be a tissue site is or includes a wound. The biofilm comprises Gram-positive bacteria and/or Gram-negative bacteria and in particular embodiments, the biofilm comprises *Staphylococcus* species such as *S. epidermidis* and *S. aureus; Candida* species such as *Candida albicans*; enterococci species such as *Enterococcus faecalis, Streptococcus* species; *P. aeruginosa; K. pneumoniae*; and diphtheroids. In a further embodiment, the method further comprises applying reduced pressure to the tissue site.

In another embodiment, the present invention provides a bifunctional ligand comprising a quorum-sensing-molecule-binding region and a protease-binding region. In a further embodiment, the present invention provides a composition comprising a bifunctional ligand and a pharmaceutically acceptable carrier. In certain embodiment, the composition comprises two or more bifunctional ligands.

The biofilm may comprise one or more of a bacteria, fungi, yeast, or protozoa. In one embodiment, the biofilm comprises Gram-positive bacteria. The Gram-positive bacteria may be, for example, one or more of *Staphylococcus aureus, Staphylococcus epidermis, Streptococcus pyogenes* (group A), *Streptococcus* species (viridans group), *Streptococcus agalactiae* (group B), *Streptococcus bovis, Streptococcus pneumoniae, Enterococcus* species, *Bacillus anthracis, Corynebacterium diphtheriae, Listeria monocytogenes, Clostridium tetani*, or *Clostridium difficile*. The Gram-positive bacteria may be selected from the group consisting of *Staphylococcus aureus, Staphylococcus epidermis, Streptococcus pyogenes* (group A), *Streptococcus* species (viridans group), *Streptococcus agalactiae* (group B), *Streptococcus bovis, Streptococcus pneumoniae, Enterococcus* species, *Bacillus anthracis, Corynebacterium diphtheriae, Listeria monocytogenes, Clostridium tetani*, and *Clostridium difficile*.

In some embodiments, the biofilm comprises Gram-negative bacteria. The Gram-negative bacteria may be, for example, one or more of *Escherichia coli, Enterobacter* species, *Proteus mirablis, Pseudomonas aeruginosa, Klebsiella pneumoniae, Salmonella* species, *Shigella* species, *Serratia* species, *Campylobacter jejuni* species, *Neisseria* species, or *Branhamella catarrhalis*. The Gram-negative bacteria may be selected from the group consisting of *Escherichia coil, Enterobacter* species, *Proteus mirablis, Pseudomonas aeruginosa, Klebsiella pneumoniae, Salmonella* species, *Shigella* species, *Serratia* species, *Campylobacter jejuni* species, *Neisseria* species, and *Branhamella catarrhalis*.

The surface being treated may be any surface on which a biofilm has formed or may form. In certain aspects of the invention, the surface is living tissue. In some embodiments, living tissue is in contact with an object such as an indwelling medical device or a wound dressing. Non-limiting examples of indwelling medical devices include catheters, ventilation tubes, and feeding tubes. In some embodiments, the biofilm and/or the surface is located in a wound.

The quorum-sensing-molecule-binding region of the bifunctional ligand is a region that binds quorum-sensing molecules. The quorum sensing molecule may be of bacterial origin, fungal origin, including yeast origin, or protozoa origin. Non-limiting examples of quorum-sensing molecules include acylated homoserine lactones (AHLs), autoinducing peptides (AIP), AI-2 (a furanosyl borate diester), γ-butyrolactones, or competence stimulating peptide (CSP). The quorum-sensing-molecule-binding region of the bifunctional ligand may be a small molecule, RNA- or DNA-based aptamer, or it may be derived from the naturally occurring transporter, receptor, or sensor of the quorum-sensing molecule. For example, LuxR is a sensor of AHL, ABC exporter and AgrC transmembrane sensor kinase bind AIP, Lsr ABC-type transporter and LuxQ transmembrane sensor kinase bind AI-2, ArpA binds γ-butyrolactone, and ComAB and ComD transmembrane sensor kinase bind CSP. Alternatively, the quorum-sensing-molecule-binding region of the bifunctional ligand may be a peptide or an antibody or antibody fragment that binds the quorum-sensing molecule.

The protease-binding region of the bifunctional ligand is a region that binds a protease capable of hydrolyzing a quorum-sensing peptide. In certain aspects, the protease is derived from a microbe, such as a bacteria, fungi, or protozoa. In certain embodiments, the protease is a lactonase (also known as acyl-homoserine lactonase). The protease-binding region may be a peptide or an antibody or antibody fragment that binds the quorum-sensing molecule.

The regions of the bifunctional ligand may be chemically joined. In certain aspects, it may be desirable to include a linker or spacer between the regions in order to, for example, reduce steric hindrance between the two regions.

In some embodiments, the bifunctional ligands may be provided in a variety of forms, particularly forms suitable for topical delivery to wound sites or application to medical devices that will be in contact with tissues. For example, the bifunctional ligand may be applied by coating the tissue with a liquid, gel, or foam formulation and injected into the tissue site. The bifunctional ligand may also be applied on or around medical devices inserted in the body. The wound may be covered with a wound dressing after the bifunctional ligand is applied. In certain aspects, the wound dressing comprises the bifunctional ligand (e.g., foam comprising the bifunctional ligand or gauze soaked in or coated with the bifunctional ligand), in which case the bifunctional ligand may be applied to the wound by applying the wound dressing to the wound.

The composition may also include additional active ingredients, such as a protease or an additional antibiotic agent. The compositions disclosed herein may be provided in a kit.

It has been reported that sub-inhibitory concentrations of antimicrobial agents may induce biofilm formation (e.g., Frank et al., 2007). In view of this, the lethal dosage for treatment of biofilm-forming microorganisms may be significantly higher than the standard therapeutically effective amount determined for planktonic microorganisms (i.e., a lethal amount or a lethal dosage) typically used by one of ordinary skill in the art. Thus, the "standard therapeutically effective" amount would be the amount of antimicrobial agent necessary to treat biofilm-forming microorganisms. A "standard therapeutic amount" or "standard therapeutic dose" may also refer to an amount of an agent sufficient to reduce or eliminate planktonic microorganisms. In some embodiments, treatment of biofilms and biofilm-forming microorganisms may require two or more doses of the bifunctional ligand.

In some embodiments the bifunctional ligand is used in combination with other treatments. For example, in one embodiment, the method of treatment comprises contacting the biofilm or the surface with the bifunctional ligand and a protease or an additional antibiotic agent. Where the area being treated is at a tissue site, the treatment may further comprise applying reduced pressure to a wound.

The term "tissue site" as used herein includes, without limitation, a wound or defect located on or within any tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location. The tissue may be that of any mammal, such as a mouse, rat, rabbit, cat, dog, pig, or primate, including humans, that are being treated as patients. Also, the wound at the tissue site may be due to a variety of causes, including trauma, surgery, degeneration, and other causes.

The term "medical indwelling device" refers to any medical device implanted or inserted in the human body. Such devices can be temporarily or permanently implanted or inserted.

It is contemplated that any method or composition described herein can be implemented with respect to any other method or composition described herein.

The term "reduced pressure" as used herein generally refers to a pressure less than the ambient pressure at a tissue site that is being subjected to treatment. In most cases, the reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained.

Instillation of a tissue site, which generally refers to the slow introduction of a solution to the tissue site, can expose a tissue site to temperature variations, drugs, or other substances that may further promote healing or growth of tissue. Instillation may also be referred to as irrigation or infusion in some contexts. Instillation may be continuous or intermittent and may take place prior to, subsequent to, or simultaneously with the application of reduced pressure. In some embodiments, instillation and negative pressure may be coordinated by a central controller.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
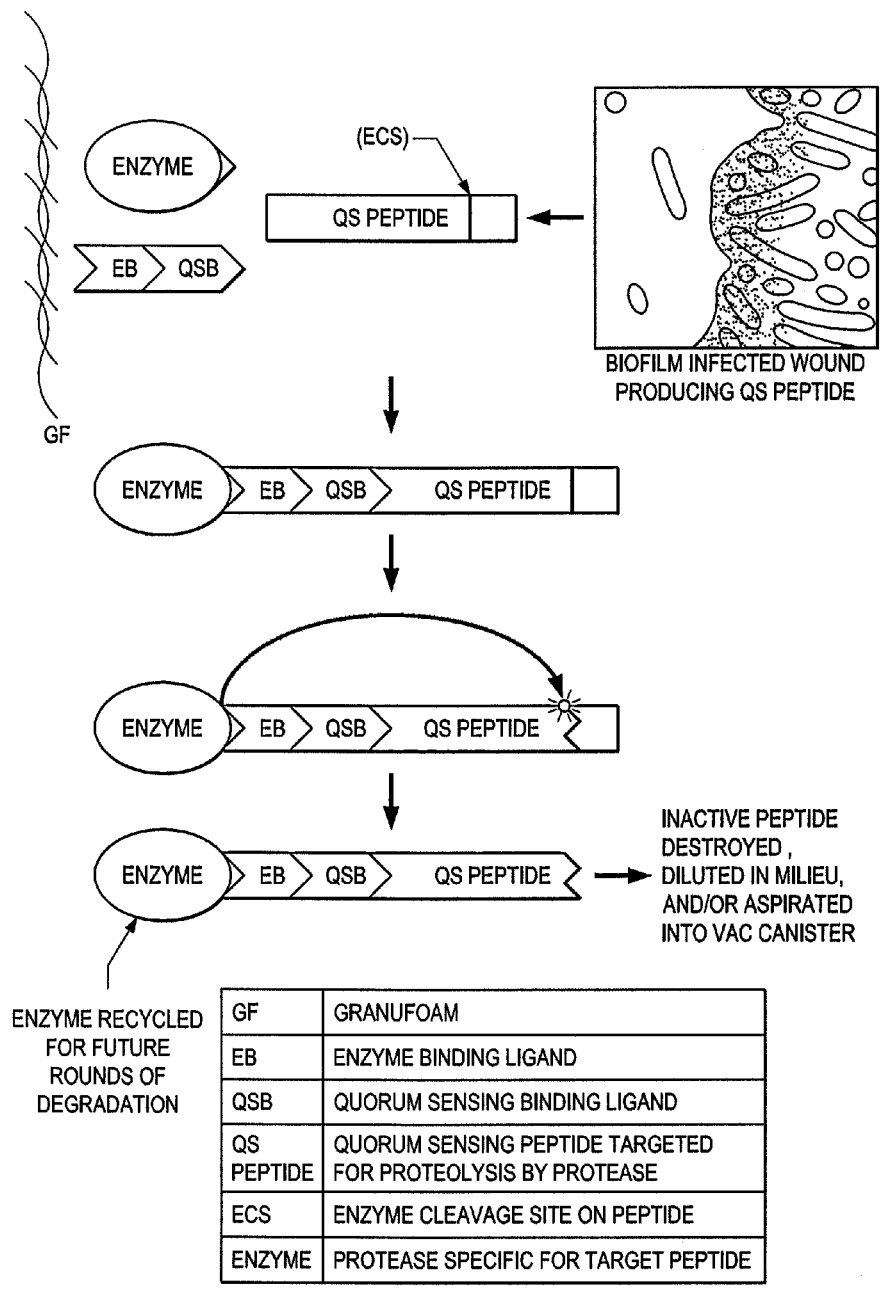
FIG. 1. Targeted enzymatic degradation of quorum-sensing peptides using a bifunctional ligand.

A biofilm forms when microorganisms adhere to each other and to a surface, and produce extracellular polymers that facilitate adhesion and provide a structural matrix. This surface may be living tissue or inert, nonliving material. Formation of the biofilm begins with the initial attachment of microorganisms to a surface. The attachment is initially through weak, reversible adhesion, but the microorganisms will proceed to anchor themselves more permanently using cell adhesion structures such as pili if they are not removed from the surface. Other cells then arrive to build the matrix that holds the biofilm together. Some species are not able to attach to a surface on their own, but are able to anchor themselves to the matrix or directly to earlier colonists. Thus, the early colonists provide adhesion sites that facilitate the adhesion of additional cells.

During colonization, the cells communicate via quorum sensing, which is a system of stimulus and response correlated to population density. A variety of different molecules can be used as signals in quorum sensing. These signaling molecules are also referred to as "quorum-sensing molecules," "inducer molecules," or "autoinducers." Microbes also have receptors that "sense" the presence or absence of quorum-sensing molecules. Common classes of quorum-sensing molecules include N-Acyl Homoserine Lactones (AHL) in Gram-negative bacteria, and a family of autoinducers known as autoinducer-2 (AI-2) in both Gram-negative and Gram-positive bacteria.

*P. aeruginosa*, for example, relies on quorum sensing via production of signaling molecules such as lactones N-butanoyl-1-homoserine (C4-HSL) and N-(3-oxododecanoyl)-1-HSL (3-oxo-C12-HSL) (Smith et al. (2003) *Current Opinion in Microbiology* 1(1): 56-60). Although multiple signaling molecules may be involved in quorum sensing, the absence of just one component of the quorum-sensing system can result in a significant reduction in biofilm formation.

As mentioned above, the microorganisms also have receptors for the signaling molecules. For example, the receptor LuxP is a receptor for AI-2. When the signaling molecule binds the receptor, it activates transcription of certain genes, including those for signaling molecule synthesis forming a positive feedback loop.

Quorum quenching may be achieved by degrading the signaling molecule, such as with a protease. Lactonase (also known as acyl-homoserine lactonase) is a metalloenzyme that targets and inactivates acylated homoserine lactones (AHLs). Lactonase hydrolyzes the ester bond of the homoserine lactone ring of acylated homoserine lactones. By hydrolysing AHL, lactonase prevents these signaling molecules from binding to their target transcriptional regulators, thereby inhibiting quorum sensing. Lactonases have been reported for *Bacillus, Agrobacterium, Rhodococcus, Streptomyces, Arthrobacter, Pseudomonas*, and *Klebsiella* (Schipper et al. (2009) *Molecular Plant-Microbe Interactions* 75: 224-233). The *Bacillus cereus* group (*B. cereus, B. thuringiensis, B. mycoides,* and *B. anthracis*) was found to contain nine genes homologous to the AiiA gene that encode AHL-inactivating enzymes (Dong et al. (2002). *Applied and Environmental Microbiology* 68(4): 1754-1759). Some examples of lactonases are AiiA produced by *Bacillus* species, AttM and AiiB produced by *Agrobacterium tumefaciens*, and QIcA produced by *Rhizobiales* species (Riaz et al. (2008) *Environmental Microbiology* 10(3): 560-570). The direct therapeutic application of lactonases is complicated by the fact that lactonolysis is a reversible reaction (Rasmussen and Givskov (2006) *International Journal of Medical Microbiology* 296 (2-3):149-161). The bifunctional ligand disclosed herein provides a solution to this problem by targeting proteases, such as lactonases, to the quorum sensing signaling molecules and thereby mediating irreversible degradation of the molecule.

Biofilm-associated microorganisms behave differently from planktonic organisms. Additionally, biofilms are characterized by their ability to become increasingly resistant to antimicrobial treatments. Resistance of biofilms to antimicrobial agents is believed to be due to the extracellular matrix in which the bacterial cells are embedded providing a barrier toward penetration by the biocides (Costerton et al., 1999). However, it is also possible that a majority of the cells in a biofilm are in a slow-growing, nutrient-starved state, and therefore not as susceptible to the effects of anti-microbial agents. Additionally, the resistance to antimicrobial agents may be due to the cells in a biofilm adopting a distinct and protected biofilm phenotype, e.g., by elevated expression of drug-efflux pumps. Antimicrobial concentrations sufficient to inactivate planktonic organisms are generally inadequate to inactivate biofilm organisms, especially those deep within the biofilm. Biofilm formations also make it difficult for host phagocytic cells to gain access to and kill the organisms.

Biofilms can be comprised of bacteria, fungi, yeast, protozoa, and other microorganisms. Biofilms may be composed of single species or multiple species of microorganism. The most common biofilms have been found to be bacterial biofilms. Both Gram-negative and Gram-positive bacteria are capable of forming biofilms. Examples of Gram-positive bacteria that are capable of forming biofilms include, but are not limited to, *Staphylococcus aureus*, coagulase negative staphylocci such as *Staphylococcus epidermis, Streptococcus pyogenes* (group A), *Streptococcus* species (viridans group), *Streptococcus agalactiae* (group B), *S. bovis, Streptococcus* (anaerobic species), *Streptococcus pneumoniae*, and *Enterococcus* species. Other Gram-positive bacilli capable of forming biofilms include *Bacillus anthracis, Corynebacterium diphtheriae* and *Corynebacterium* species which are diptheroids (aerobic and anerobic), *Listeria monocytogenes, Clostridium tetani*, and *Clostridium difficile*. Examples of Gram-negative bacteria that are capable of forming biofilms are bacteria from the genus *Escherichia coli, Enterobacter* species, *Proteus mirablis* and other species, *Pseudomonas aeruginosa, Klebsiella pneumoniae, Salmonella, Shigella, Serratia*, and *Campylobacterjejuni, Neisseria* and *Branhamella catarrhalis*.

Additional organisms capable of forming biofilm may include dermatophytes (*Microsporum canis* and other *M.* spp.; and *Trichophyton* spp. such as *T. rubrum*, and *T. mentagrophytes*), yeasts (e.g., *Candida albicans, C. Parapsilosis, C. glabrata, C. tropicalis*, or other *Candida* species including drug resistant *Candida* species), *Epidermophytonfloccosum, Malassezia fuurfur* (*Pityropsporon orbiculare*, or *P. ovale*), *Cryptococcus neoformans, Aspergillus fumigatus*, and other *Aspergillus* spp., *Zygomycetes* (*Rhizopus, Mucor*), hyalohyphomycosis (*Fusarium* Spp.), *Paracoccidioides brasiliensis, Blastomyces dermatitides, Histoplasma capsulatum, Coccidioides immitis*, and *Sporothrix schenckii*.

Infections due to biofilm growth formation are common complications of wound healing and surgical procedures, particularly in patients with devitalized tissue and decreased immunity. The organisms causing biofilm growth formation that are most commonly isolated from indwelling medical devices include *Staphylococcus* species such as *S. epidermidis* and *S. aureus*; *Candida* species such as *Candida albicans*; enterococci species such as *Enterococcus faecalis, Streptococcus* species; *P. aeruginosa; K. pneumoniae*; and diphtheroids. These organisms may originate from the skin of patients or healthcare workers, tap water to which entry ports are exposed, or other sources in the environment.

The predilection of *Pseudomonas aeruginosa* to form biofilms is a major contributing factor to the problems of biofilm growth formation in the medical and industrial environments. *P. aeruginosa* is highly associated with biofilm growth and catheter obstruction. For example, biofilms of *P. aeruginosa* have been isolated from medical implants, such as indwelling urethral, venous or peritoneal catheters (Stickler et al., 1998). Burn wounds often become infected with *P. aeruginosa* from which life-threatening invasion of the blood stream and septic shock can arise. These infections are believed to involve the formation of biofilms. Thus, topical application to the wounds of a bifunctional ligand composition as described herein can be used in to inhibit initiation of infection by preventing or inhibiting biofilm formation.

As discussed above, the bifunctional ligands disclosed herein comprise a first region that binds to a quorum-sensing molecule and a second region that binds a protease. The quorum-sensing-molecule-binding region of the bifunctional ligand may be a small molecule or derived from, for example, the naturally occurring receptor of the quorum-sensing molecule or an antibody or antibody fragment that binds the quorum-sensing molecule. The protease-binding region binds a protease capable of hydrolyzing the quorum-sensing molecule that binds to the quorum-sensing-molecule-binding region of the bifunctional ligand.

Quorum-sensing molecules include, for example, acylated homoserine lactones (AHLs), autoinducing peptides (AIP), AI-2 (a furanosyl borate diester), γ-butyrolactones, or competence stimulating peptide (CSP). Various microbes may use the above-mentioned quorum-sensing systems. Non-limiting examples of bacteria that use each of the above-mentioned systems are: *Vibrio fischeri* (AHL), *Staphylococcus aureus* (AIP), *Vibrio harveyi* (AI-2), *Streptomyces griseus* (γ-butyrolactone), and *Streptococcus pneumonia* (CSP). The quorum-sensing-molecule-binding region of the bifunctional ligand may be a small molecule or it may be derived from the naturally occurring transporter, receptor, or sensor of the quorum-sensing molecule. For example, LuxR is a sensor of AHL, ABC exporter and AgrC transmembrane sensor kinase bind AIP, Lsr ABC-type transporter and LuxQ transmembrane sensor kinase bind AI-2, ArpA binds γ-butyrolactone, and ComAB and ComD transmembrane sensor kinase bind CSP. Alternatively, the quorum-sensing-molecule-binding region of the bifunctional ligand may be a peptide or an antibody or antibody fragment that binds the quorum-sensing molecule.

The protease-binding region may, for example, bind a lactonase. Lactonases are metalloenzymes that target and inactivate acylated homoserine lactones (AHLs). Accordingly, a bifunctional ligand may comprise a quorum-sensing-molecule-binding region that binds an AHL and a protease-binding region that binds a lactonase that hydrolyzes the AHL. Such a bifunctional ligand would, therefore, promote the interaction of lactonase and AHL. By hydrolysing AHL, lactonase prevents these signaling molecules from binding to their target transcriptional regulators, thereby inhibiting quorum sensing. Lactonases have been reported for *Bacillus, Agrobacterium, Rhodococcus, Streptomyces, Arthrobacter, Pseudomonas*, and *Klebsiella* (Schipper et al. (2009) *Molecular Plant-Microbe Interactions* 75: 224-233). The *Bacillus cereus* group (*B. cereus, B. thuringiensis, B. mycoides*, and *B. anthracis*) was found to contain nine genes homologous to the AiiA gene that encode AHL-inactivating enzymes (Dong et al. (2002) *Applied and Environmental Microbiology* 68 (4): 1754-1759). Some examples of lactonases are AiiA produced by *Bacillus* species, AttM and AiiB produced by *Agrobacterium tumefaciens*, and QlcA produced by *Rhizobiales* species (Riaz et al. (2008) *Environmental Microbiology* 10 (3): 560-570).

The bifunctional ligand may further comprise a linker region between the quorum-sensing-molecule-binding region and the protease-binding region. The linker can be used to modify the distance and flexibility between the quorum-sensing-molecule-binding region and the protease-binding region. The linker may be, for example, a peptide of about 1 to about 50 amino acids in length.

The bifunctional ligands may be produced by techniques know to those in the art. For example, the bifunctional ligands may be prepared by chemical synthesis, recombinant DNA techniques, or by chemical linkage of the domains.

As discussed above, the quorum-sensing-molecule-binding region of the bifunctional ligand may comprise a small molecule. A small molecule is a low molecular weight (less than approximately 800 Daltons) organic compound. Small molecules are not polymers, but they may bind to polymers such as proteins. High-through put screening of small molecule libraries may be performed to identify small molecules that bind a particular quorum-sensing molecule. A wide variety of small molecule libraries are available from commercial vendors as well as through the National Institutes of Health. Alternatively, one may create a small molecule library using, for example, combinatorial synthesis methods. A variety of assay formats are known for screening small molecule libraries, and these assays may be employed for identifying small molecules that bind quorum-sensing molecules.

One approach for identifying a suitable protease-binding region is phage display. Phage display is a well-known technique that uses bacteriophages for the high-throughput study of protein-protein interactions. Using phage display, large libraries of proteins can be screened for their ability to bind a particular protease.

The bifunctional ligands may be provided in a variety of forms, particularly forms suitable for topical delivery to wound sites or application to medical devices that will be in contact with tissues. For example, the bifunctional ligand may be formulated in a pharmaceutical composition. The bifunctional ligand may be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, sprays, hydrogels, or electroporation device cartridges. In some embodiments, the formulation may be a hydrophilic solution, a thixotropic spray, or other hydrophillic topical. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product. In still other aspects, the formulation may be immobilized on a surface, such as a dressing, and activated by a glucose wash.

The composition may be applied through infusion within, injection into, absorption by, layering on, encapsulation within, or coating on, a carrier material, such as a bandage, gauze, wound dressing, adhesive bandage, scaffold, or hydrogel, for instance, comprising cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols) as well as gelatin. For example, a bifunctional ligand composition may be applied to a woven, non-woven, or knitted fabric material, such as gauze, dispersed within film, sponge, or foam for sustained release at a tissue site. A "carrier material" as used herein refers to a material suitable for a bifunctional ligand composition. The carrier material may be either bioresorbable, for instance comprising polyglycolic acid, polylactic acid, polydioxanone, polyhydroxybutyrate, polyhydrozyvalerate, polyaminoacids polyorthoesters, polyvinly alcohol, collagen, gelatin, chitosan, oxidized regenerated cellulose, hyaluronic acid, alginate or derivatives thereof, or may be non-bioresorbable, comprising for instance, polyurethane, polyvinyl alcohol, or gauze. In certain aspects, the composition may be bound to the carrier material, such as through hydrogen binding, covalent binding or ionic binding.

Additionally, the bifunctional ligand may be formulated in a composition with one or more additional active ingredients. For example, the bifunctional ligand may be formulated in a composition with one or more antibiotics. Such a formulation will be advantageous in treating or preventing infection because the bifunctional ligand will inhibit biofilm formation thus allowing the antibiotic to more effectively kill the microbes. Additionally, two or more different bifunctional ligands may be combined in a composition. The composition may also be an instillation composition. The compositions may be delivered to a tissue site by continuous instillation and/or periodic instillation. The instillant provides fresh bifunctional ligand to a tissue site such as a wound.

The method for applying the bifunctional ligand to tissue site or wound may vary depending on factors such as the location and the size and shape of the area to be treated. A health care provider will be able to determine an appropriate method for applying the bifunctional ligand to the area in view of such factors.

The treatment methods of the present invention may be used on their own or in combination with additional methods of treatment. In order to increase the effectiveness of a treatment with the compositions and methods of treatment of the present invention or to augment the protection of another (second) therapy, it may be desirable to combine these compositions and methods with other agents and methods effective in the treatment, reduction of risk, or prevention of infections, for example, anti-bacterial, anti-viral, and/or anti-fungal treatments. As another example, iontophoresis can be used to drive agents into tissues for the purpose of labeling or eradicating biofilms.

Yet another example would be the use of the treatment integrated with negative pressure wound therapy (NPWT), such as V.A.C.® Therapy (KCI International, San Antonio, Tex.), fluid instillation therapy, or both. Clinical studies and practice have shown that NPWT can augment and accelerate growth of new tissue at a tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as NPWT, but is also known by other names, including "negative-pressure therapy," "reduced-pressure wound therapy," "vacuum therapy," and "vacuum-assisted closure," for example. Negative-pressure therapy may provide a number of benefits, including migration of epithelial and subcutaneous tissues, improved blood flow, and micro-deformation of tissue at a tissue site. Together, these benefits can increase development of granulation tissue and reduce healing times.

Instillation of a tissue site, which generally refers to the slow introduction of a solution to the tissue site, can expose a tissue site to temperature variations, drugs, or other substances that may further promote healing or growth of tissue. Instillation may also be referred to as irrigation or infusion in some contexts. Instillation may be continuous or intermittent and may take place prior to, subsequent to, or simultaneously with the application of negative pressure. In some embodiments, instillation and negative pressure may be coordinated by a central controller.

Figure 2:
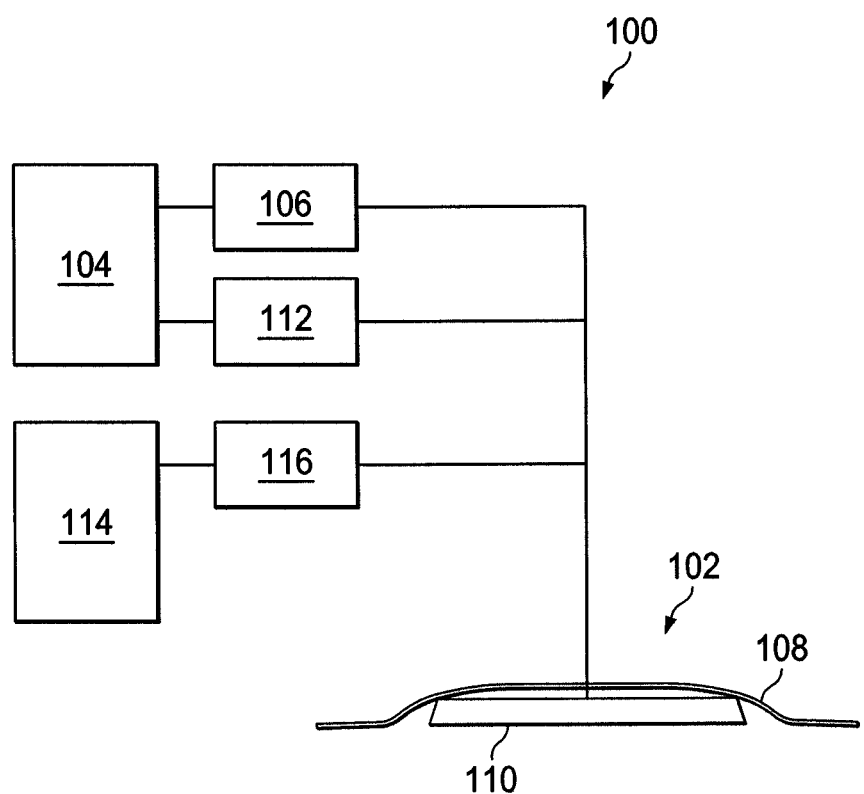
FIG. 2 shows a block diagram of a representative embodiment of a therapy system.

FIG. 2 is a simplified functional block diagram of an example embodiment of a therapy system 100 that can provide therapeutic pressure and instillation in accordance with this specification. As illustrated, the therapy system 100 may include a dressing 102 fluidly coupled to a negative-pressure source 104. A regulator or controller, such as regulator 106, may also be fluidly coupled to the dressing 102 and the negative-pressure source 104. The dressing 102 generally includes a drape, such as drape 108, and a manifold, such as distribution manifold 110. The therapy system 100 may also include fluid containers, such as container 112 and container 114, coupled to the dressing 102. As illustrated in FIG. 2, container 112 may be also be fluidly coupled to the negative-pressure source 104 in some embodiments, and container 114 may be coupled to a fluid-delivery device, such as a pump 116.

In general, components of the therapy system 100 may be coupled directly or indirectly. For example, the negative-pressure source 104 may be directly coupled to regulator 106 and indirectly coupled to dressing 102 through regulator 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the distribution manifold 110 may be placed within, over, on, or otherwise proximate to a tissue site. The drape 108 may be placed over the distribution manifold 110 and sealed to tissue proximate to the tissue site. The tissue proximate to the tissue site is often undamaged epidermis peripheral to the tissue site. Thus, the dressing 102 can provide a sealed therapeutic environment proximate to a tissue site, substantially isolated from the external, ambient environment. The negative-pressure source 104 can reduce the pressure in the sealed therapeutic environment, and the pump 116 can apply therapeutic solutions, including the embodiments of the bifunctional ligand compositions described herein. Reduced pressure and/or fluids can be applied substantially uniformly through the distribution manifold 110 in the sealed therapeutic environment. Reduced pressure can induce macrostrain and microstrain in the tissue site, as well as remove exudates and other fluids from the tissue site, which can be collected in the container 112 and disposed of properly.

Integrating negative pressure therapy and instillation therapy with embodiments of bifunctional ligand compositions described herein can further promote healing and growth of tissue by removing barriers to normal healing, such as the presence of biofilm and biofilm-forming bacteria. Functionally coupling infusion of the composition with reduced pressure therapy as disclosed herein provides unexpected decreases in wound bioburden and wound healing trajectories. The ability of a gelatin-based composition to operate with a reduced pressure therapy system allows for the use of the composition as an instillate to treat a tissue site, in particular a chronic wound, with a composition that treats and/or inhibits biofilm formation.

In some embodiments, the negative pressure with the bifunctional ligand composition can be applied during debridement of a tissue site, for example, by using a dressing having a self-contained debriding mechanism such as ultrasound or pulsed lavage. Alternatively, negative pressure therapy may be applied after debridement, to promote vascular stimulation and the formation of granulation tissue. Further still, the transition from debridement to negative pressure therapy is seamless, as well as from negative pressure therapy to passive infusion with the composition, that is, without disrupting the integrity of the tissue site.

The negative pressure with the bifunctional ligand composition may also be applied during cleansing or irrigation of the wound in some embodiments. Alternatively, the negative pressure may be applied prior to or after the cleansing of the wound with the composition.

The compositions provided herein can be used in conjunction with all current NPWT devices, and delivered in either the inpatient or outpatient setting. Exemplary negative pressure devices include V.A.C.® Therapy, V.A.C.® Instill, or V.A.C.® Ulta therapy systems (Kinetic Concepts, Inc.). These devices, or devices having similar or equivalent designs may be used.

As noted previously, "reduced pressure" or "negative pressure" generally refer to a pressure less than a local ambient pressure, such as the ambient pressure in a local environment external to a sealed therapeutic environment provided by the dressing 102. In many cases, the local ambient pressure may also be the atmospheric pressure in the vicinity of a tissue site. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 104, may be a reservoir of air maintained at a reduced pressure, or may be a manual or electrically-powered device that can reduce the pressure in a sealed volume, such as a vacuum pump, a suction pump, a wall suction port available at many healthcare facilities, or a micro-pump, for example. A reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A fluid-delivery device, such as the pump 116, may be a rotary-delivery pump, or other pump that can supply an instillation solution to a sealed space or the distribution manifold 110. A fluid-delivery device may be housed within a therapy device or used in conjunction with other components, such as sensors, processing units, alarm indicators, memory, databases, software, display devices, or user interfaces that further facilitate instillation therapy. In some embodiments, a fluid-delivery device and a negative-pressure source may be integrated into a single unit to provide both negative pressure and instillation, or to alternatingly supply negative pressure and instillation.

A manifold, such as the distribution manifold 110, can generally be adapted to contact a tissue site. The distribution manifold 110 may be adapted to be placed partially or fully in contact with the tissue site. If the tissue site is a wound, for example, the distribution manifold 110 may partially or completely fill the wound, or may be placed over the wound. The distribution manifold 110 may take many forms, and may be many sizes, shapes, or thicknesses depending on a variety of factors, such as the type of treatment being implemented or the nature and size of a tissue site. For example, the size and shape of the distribution manifold 110 may be adapted to the contours of deep and irregular shaped tissue sites.

More generally, a manifold is a substance or structure adapted to distribute negative pressure to or remove fluids from a tissue site, or both. In some embodiments, though, a manifold may also facilitate delivering fluids to a tissue site, if the fluid path is reversed or a secondary fluid path is provided, for example when instillation solution is applied. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, cellular foam, open-cell foam, porous tissue collections, and other porous material such as gauze or felted mat generally include structural elements arranged to form flow channels. Liquids, gels, and other foams may also include or be cured to include flow channels.

In one illustrative embodiment, the distribution manifold 110 may be a porous foam material having interconnected cells or pores adapted to uniformly (or quasi-uniformly) distribute reduced pressure to a tissue site. The foam material may be either hydrophobic or hydrophilic. In one non-limiting example, the distribution manifold 110 may be an open-cell, reticulated polyurethane foam such as GranuFoam® dressing available from Kinetic Concepts, Inc. of San Antonio, Tex.

In some embodiments, such as embodiments in which the distribution manifold 110 may be made from a hydrophilic material, the distribution manifold 110 may also wick fluid away from a tissue site while continuing to distribute reduced pressure to the tissue site. The wicking properties of the distribution manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 110 may further promote granulation at a tissue site if pressure within a sealed therapeutic environment is reduced. For example, any or all of the surfaces of the distribution manifold 110 may have an uneven, coarse, or jagged profile that can induce microstrains and stresses at a tissue site if reduced pressure is applied through the distribution manifold 110.

In one example embodiment, the distribution manifold 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones.

Other bioresorbable materials that may be used include, but are not limited to, polydioxanone, polyhydroxybutyrate, polyhydrozyvalerate, polyaminoacids polyorthoesters, polyvinly alcohol, chitosan, oxidized regenerated cellulose, hyaluronic acid, alginate, collagen, a modified collagen, such as gelatin or derivatives of any of the above.

The distribution manifold 110 may further serve as a scaffold for new cell-growth, or a scaffold material may be used in conjunction with the distribution manifold 110 to promote cell-growth. In general, a scaffold material may be a substance or structure used to enhance or promote the growth of cells or formation of tissue, such as a three-dimensional porous structure that provides a template for cell growth.

A scaffold and/or manifold may be also be infused with, coated with, or comprised of cells, growth factors, extracellular matrix components, nutrients, integrins, or other substances to promote cell growth in addition to embodiments of the compositions described herein. The manifold or scaffold may serve as a carrier material for the composition described herein.

Scaffolds may be formed from biologic or synthetic scaffold materials, and are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. Nonlimiting examples of suitable scaffold materials include extracellular matrix proteins such as fibrin, collagen or fibronectin, and synthetic or naturally occurring polymers, including bioabsorbable or non-absorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes (e.g., GranuFoam®), polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon.

The scaffold can also comprise ceramics such as hydroxyapatite, corallin apatite, calcium phosphate, calcium sulfate, calcium carbonate or other carbonates, bioglass, allografts, autografts, xenografts, decellularized tissues, or composites of any of the above. In some embodiments, the scaffold may comprise collagen (e.g., Biostep™ or Pomogran™ scaffolds), polylactic acid (PLA), polyglycolic acid (PGA), polylactide-co-glycolide (PLGA), a polyurethane, a polysaccharide, an hydroxyapatite, or a polytherylene glycol. Additionally, the scaffold can comprise combinations of any two, three or more materials, either in separate or multiple areas of the scaffold, combined noncovalently or covalently (e.g., copolymers such as a polyethylene oxide-polypropylene glycol block copolymers, or terpolymers), or combinations thereof.

The drape 108 is an example of a sealing member. A sealing member may be constructed from a material that can provide a fluid seal between two environments or components, such as between a therapeutic environment and a local external environment. The sealing member may be, for example, an impermeable or semi-permeable, elastomeric material that can provide a seal adequate to maintain a negative pressure at a tissue site for a given negative-pressure source. For semi-permeable materials, the permeability generally should be low enough that a desired negative pressure may be maintained. An attachment device may be used to attach a sealing member to an attachment surface, such as undamaged epidermis, a gasket, or another sealing member. The attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The container 114 is representative of another container, canister, pouch, cartridge, or other storage component, which can be used to manage instillation solution to be supplied to a tissue site. In many environments a rigid container may be preferred or required for delivering, storing, and supplying of the instillation solution. In other environments, instillation solution may be provided in a non-rigid container, and a re-usable container could reduce waste and costs associated with instillation.

Components of therapy system 100 may also be provides as one or more kits. In one embodiment, for example, a kit comprises components for inhibiting biofilms. Any of the components disclosed here in may be combined in a kit. In certain embodiments, the kit comprises a biofilm-inhibiting composition disclosed herein. The kit may further comprise a wound dressing, such as a gauze, cloth, or film.

The kits will generally include at least one vial, test tube, flask, bottle, syringe, foil package, or other container, into which a component may be placed, and preferably, suitably aliquoted. Where there is more than one component in the kit, the kit also will generally contain a second, third or other additional containers into which the additional components may be separately placed. However, various combinations of components may be comprised in a container. The kits of the present invention also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

The effectiveness of the treating a biofilm or inhibiting biofilm-formation may be determined using methods known in the art. One method is to extract any bacteria remaining in the biofilm after treatment, plating the bacteria on a suitable media and allowing the bacteria to grow for 24-48 hours or as appropriate, then counting any bacteria. A reduction in bacteria is reflects effectiveness of the bifunctional ligand and the method of treatment. Alternatively, treatment between groups using in vitro methods such as described in Phillips et al., "Effects of antimicrobial Agents on an in vitro biofilm model of skin wounds," *Advances in Wound Care*, 1:299-304 (2010), or as otherwise known in the art.

EXAMPLES

Example I

A subject is identified as having a wound that has become infected with *S. aureus* that has formed a biofilm in the wound. The wound is treated with a bifunctional ligand that comprises a first region that binds to a quorum-sensing molecule and a second region that binds a protease with a standard therapeutically effective amount for a period of time sufficient to reduce biofilm in the wound.

Example II

A subject is identified as having a wound that has become infected with a *P. aeruginosa* that has formed a biofilm in the wound. The wound is treated with a bifunctional ligand that comprises a first region that binds to a quorum-sensing molecule and a second region that binds a protease with a standard therapeutically effective amount for a period of time in combination with VAC® Therapy at −125 mmHg to reduce biofilm in the wound.

Example III

*P. aeruginosa* forms a biofilm on a ventilation tube. The ventilation tube is treated with a bifunctional ligand that comprises a first region that binds to a quorum-sensing molecule and a second region that binds a protease in an amount and for a period of time sufficient to reduce the biofilm on the ventilation tube.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method for treating a biofilm and/or inhibiting biofilm formation, comprising:
contacting a biofilm or a surface with a bifunctional ligand comprising a quorum-sensing-molecule-binding region chemically linked to a protease-binding region; and
delivering reduced pressure to the biofilm or the surface;
wherein the quorum-sensing-molecule-binding region is adapted to bind one or more of acylated homoserine lactones (AHLs), autoinducing pepties (AIP), AI-2 (furanosyl borate diester), γ-butyrolactones, or competence stimulating peptide (CSP);
wherein the protease-binding region is adapted from a lactonase.

2. The method of claim 1, wherein the biofilm comprises Gram-positive bacteria.

3. The method of claim 2, wherein the Gram-positive bacteria is one or more of *Staphylococcus aureus, Staphylococcus epidermis, Streptococcus pyogenes* (group A), *Streptococcus* species (viridans group), *Streptococcus agalactiae* (group B), *Streptococcus bovis, Streptococcus pneumoniae, Enterococcus* species, *Bacillus anthracis, Corynebacterium diphtheriae, Listeria monocytogenes, Clostridium tetani,* or *Clostridium difficile*.

4. The method of claim 1, wherein the biofilm comprises Gram-negative bacteria.

5. The method of claim 4, wherein the Gram-negative bacteria is one or more of *Escherichia coli, Enterobacter* species, *Proteus* mirablis, *Pseudomonas aeruginosa, Klebsiella pneumoniae, Salmonella* species, *Shigella* species, *Serratia* species, *Campylohacter* species, *Neisseria* species, or *Branhamella catarrhalis*.

6. The method of claim 1, wherein the surface is a tissue site.

7. The method of claim 6, wherein the tissue site is in contact with an indwelling medical device.

8. The method of claim 1, wherein the surface is an indwelling medical device.

9. The method of claim 8, wherein the indwelling medical device is a catheter or a ventilation tube.

10. The method of claim 1, wherein the recombinant bifunctional ligand is formulated in a gel or a foam.

11. The method of claim 1, further comprising contacting the biofilm or the surface with an antibiotic.

12. The method of claim 1, further comprising contacting the biofilm or the surface with a protease.

13. The method of claim 1, wherein the biofilm and/or the surface is located in a wound.

14. The method of claim 1, wherein the quorum-sensing-molecule-binding region may comprise at least one of LuxR, ABC exporter, AgrC transmembrane sensor kinase, LsrABC-type transporter, LuxQ transmembrane sensor kinase, ArpA, ComAB, and ComD transmembrane sensor kinase.

15. The method of claim 1, wherein the quorum-sensing-molecule-binding region and the protease-binding region are chemically linked with a linker comprising a peptide of about 1 to about 50 amino acids in length.

* * * * *